United States Patent
Hardy

(10) Patent No.: US 12,133,759 B2
(45) Date of Patent: Nov. 5, 2024

(54) CARDIOTOCOGRAPHY GIRDLE

(71) Applicant: NATEO HEALTHCARE, Toulouse (FR)

(72) Inventor: Celine Hardy, Merenvielle (FR)

(73) Assignee: NATEO HEALTHCARE, Toulouse (FR)

( * ) Notice: Subject to any disclaimer, the term of this patent is extended or adjusted under 35 U.S.C. 154(b) by 81 days.

(21) Appl. No.: 17/797,465

(22) PCT Filed: Feb. 4, 2021

(86) PCT No.: PCT/FR2021/050211
§ 371 (c)(1),
(2) Date: Aug. 4, 2022

(87) PCT Pub. No.: WO2021/156576
PCT Pub. Date: Aug. 12, 2021

(65) Prior Publication Data
US 2023/0103987 A1    Apr. 6, 2023

(30) Foreign Application Priority Data
Feb. 4, 2020 (FR) ..................................... 2001080

(51) Int. Cl.
*A61B 8/02* (2006.01)
*A61B 8/08* (2006.01)

(52) U.S. Cl.
CPC .............. *A61B 8/02* (2013.01); *A61B 8/0883* (2013.01)

(58) Field of Classification Search
CPC ................................ A61B 8/02; A61B 8/0883
See application file for complete search history.

(56) References Cited

U.S. PATENT DOCUMENTS

| | | | |
|---|---|---|---|
| 8,911,371 B2* | 12/2014 | George | A61B 8/4281 601/3 |
| 2011/0160591 A1 | 6/2011 | Smith et al. | |
| 2013/0331704 A1 | 12/2013 | Salzman | |
| 2015/0158052 A1* | 6/2015 | Latev | B06B 1/0622 156/60 |
| 2018/0206819 A1* | 7/2018 | Saarinen | A61B 8/4444 |
| 2020/0029930 A1 | 1/2020 | Landman et al. | |
| 2023/0218274 A1* | 7/2023 | Ruiter | A61B 8/14 600/443 |

FOREIGN PATENT DOCUMENTS

| | | |
|---|---|---|
| EP | 2213241 A1 | 8/2010 |
| WO | 2004086085 A1 | 10/2004 |
| WO | 2007120873 A2 | 10/2007 |

* cited by examiner

Primary Examiner — Dixomara Vargas
(74) Attorney, Agent, or Firm — BCF LLP

(57) ABSTRACT

The invention relates to a cardiotocography girdle. It is in the form of a spherical cap and comprises at least nineteen ultrasound transducers, denoted USTs, which are positioned on a first support layer (23) made of an elastic material, each UST being positioned in a support cavity (20), said girdle comprising a second support layer (24), likewise made of an elastic material and which encapsulates said USTs housed in the support cavities (20) with the first support layer (23), assembly being performed by adhesively bonding the first support layer (23) to the second support layer (24).

9 Claims, 4 Drawing Sheets

CARDIOTOCOGRAPHY GIRDLE

CROSS-REFERENCE TO RELATED APPLICATIONS

This application is a national phase filing under 35 U.S.C. § 371 of International Application No. PCT/FR2021/050211 filed on Feb. 4, 2021, which claims priority from French Patent Application No. 2001080 filed Feb. 4, 2020, the contents of each of which are hereby incorporated by reference in their entirety.

FIELD OF THE INVENTION

The present invention to a girdle for cardiotocography (abbreviated CTG), referred to in the following as a CTG girdle.

The word "CTG" has the following meaning: cardio=heart, toco=contraction, graph=to write.

During pregnancy, the heartbeats of the child are monitored the first ultrasonography and are already audible.

This girdle is used in the field of the gynaecology-obstetrics in order to evaluate the well-being of the foetus from the 24th week of amenorrhoea, for single-foetus pregnancies and also for normal, intermediate or pathological twin pregnancies.

PRIOR ART

The CTG girdle is an instrument composed of internal and/or external sensors measuring physiological parameters of the foetus and the mother.

The recording of the foetal heart rate and uterine contractions are two indicators which help the doctor to make a clinical interpretation of foetal well-being during pregnancy and childbirth and, in particular, to detect oxygen deprivation of the foetus (perinatal asphyxia).

In general, the ultrasound sensor is placed on the maternal abdomen and its position must be optimised by the medical personnel. An elastic strap surrounding the maternal abdomen enables the sensor to be held in a fixed location and ensures good coupling.

However, poor positioning of the ultrasound sensor leads to false measurements and consequently to poor diagnostics.

An example of the prior art is document WO2004/086085 which describes a plurality of ultrasound sensors for measuring foetal heart rate. However, this document is unsatisfactory because it describes a transducer, the cover of which has the same size (diameter 8 cm/4 cm thickness) and is made of the same (rigid) plastic material as commercially available CTG sensors. This sensor is placed flat on the abdomen of the patient without elasticity or flexibility. This transducer causes the same level of discomfort and inhibition of the mobility of the patient during the measurements, as the CTG prior art mentioned above.

One objective of the invention is to ensure good positioning of a plurality of sensors. Another objective is to improve patient comfort.

DESCRIPTION OF THE INVENTION

The present invention aims to overcome these disadvantages with an entirely innovative approach.

To this effect, the present invention relates to a cardiotocography girdle characterised in that it is in the form of a spherical cap and includes at least nineteen ultrasound transducers, referred to as USTs, which are positioned on a first support layer made of an elastic material, each UST being positioned in a support cavity, said girdle comprising a second support layer, likewise made of an elastic material and which encapsulates said USTs housed in the support cavities with the first support layer, assembly being performed by adhesively bonding the first support layer to the second support layer.

According to an example, the support cavities are connected together by links in order to form a regular array of transducers.

These provisions mean that there is a unique positioning at the outset. There is no repositioning of the sensor by the medical personnel (midwife/obstetrician).

The shape of a spherical cap can be adaptable to all the morphologies of pregnant women in order to always remain in contact with the abdomen. This shape can cover a hemispherical surface.

Another advantage for the patient is having a three-dimensional shape which provides an enveloping structure and allows freedom of movement, such as standing up or sitting down, without having to reposition the girdle. The position of the girdle is fixed whatever the posture of the patient (standing, lying down, seated) or her level of activity.

Other advantages are the comfort and rapidity of the medical examination (CTG recording).

The comfort is linked to the fact that the patient is not required to remain immobile throughout the examination.

The girdle enables a one-time positioning of a sensor array on the patient without a large number of potential medical procedures. Indeed, positioning of the single sensor of the commercially available CTG (prior art) can be difficult in preterm pregnancies, because of the small size of the heart of the foetus and because the foetus can move freely in the uterus.

Once the clinician has determined this position, the sensor is fixed using an elastic strap passing around the maternal abdomen in order to allow continuous recordings of the foetal heart rate (FHR) at a specific location of the foetus heart.

However, due either to the movements of the foetus in the uterus or to the movement of the sensor on the abdomen of the mother (change in position of the mother), the FHR recordings may exhibit signal losses making them unsuitable for clinical interpretation. Consequently, the patient has to wait for the return of the medical personnel in order to proceed with a possible manual repositioning of the US sensor and a new examination.

In another example, illustrated by the figures below, the girdle includes thirty-one USTs.

The fact of having a first layer and a second layer makes the assembly sealed. This makes it cleanable. The term "sealed" means that it does not allow the passage of liquids.

Sealing is important for two reasons:
 the coupling gel (water-based gel) which is deposited by the clinicians on the USTs should not be able to infiltrate inside the technical electronic part,
 this gel must be removable after examination by simple wiping and the girdle must be able to be disinfected by passage of a wipe containing a liquid product.

The invention is advantageously implemented according to the embodiments and the alternatives disclosed below, which are to be considered individually or according to any technically feasible combination.

In an embodiment, said support cavities are arranged in the following manner, in which at least:
 five support cavities follow a central line defining a line of symmetry each separated by a rigid link, four support cavities follow a first line parallel to the central line, the first line is proximal to the central line and situated on one side, each support cavity of the first line is alternately positioned with two support cavities of the central line and connected to each of the two support cavities of the central line by a rigid link, four support cavities follow a second line parallel to the central line, the second line is proximal to the central line and situated on the other side of the central line, each support cavity of the second line is alternately positioned with two support cavities of the central line and connected to each of the two support cavities of the central line by a rigid link, three support cavities follow a third line parallel to the central line, the third line is distal from the central line and situated on the side of the first line, each support cavity of the third line is alternately positioned with two support cavities of the first line and connected to each of the two support cavities of the first line by a rigid link, three support cavities follow a fourth line parallel to the central line, the fourth line is distal from the central line and situated on the side of the second line, each support cavity of the fourth line is alternately positioned with two support cavities of the second line and connected to each of the two support cavities of the second line by a rigid link.

The term rigid means the fact of having a link between two support cavities, this link is, according to one example, made of thermoplastic material which allows a certain flexibility.

In an embodiment, the thickness of the first layer or the second support layer is between 1 and 2 mm, preferably between 1.3 and 1.7 mm.

In an embodiment, the proximal distance between the first line and the central line, or between the second line and the central line, is between 32 and 40 mm. The distances should be understood as the spacing between the centres of the transducers.

The spacing between sensors should not be greater than 45 mm (with a tolerance of 1 mm) because this will generate cardiac areas that are potentially not covered by the ultrasound field.

In an embodiment, the distal distance between the third line and the central line, or between the fourth line and the central line, is between 64 and 80 mm.

In an embodiment, the rigid link between the central line and the first line, or between the central line and the second line, forms an angle of between 50 and 70° with respect to the central line.

In an embodiment, the rigid link between the first line and the third line, or between the second line and the fourth line, forms an angle of between 50 and 70° with respect to the central line.

In an embodiment, each rigid link has a length between 38 and 46 mm.

In an embodiment, the elastic material is silicone.

In an embodiment, a (marker) through-hole is located between the first line and the central line, said through-hole is substantially in a central position of said girdle. The technical effect is that this through-hole facilitates the positioning of the girdle by the user. During positioning of the girdle, the user or the practitioner uses the through-hole as a marker hole for locating the patient's navel. When the girdle includes the second support layer, the through-hole is sealed and does not allow liquids to pass between the first support layer and the second support layer.

In an embodiment, the through-hole is substantially in a central position of said girdle. In this alternative, the hole is independent of the position of the lines defined above. However, the associated technical effects remain unchanged. Advantageously, the (marker) through-hole is located in a region of the girdle which corresponds to a typical position of patients' navels, when the girdle is correctly position. Hence, the marker hole can indicate that the girdle is correctly positioned on the patient. Advantageously, the marker hole has a diameter slightly larger than a human index finger, in other words 10 to 12 mm.

The marker hole is independent of the number, shape or position of the transducers.

BRIEF DESCRIPTION OF THE FIGURES

Other advantages, aims and features of the present invention arise from the description which follows, given for the purposes of explanation and in no way limiting, with reference to the appended drawings, in which.

DESCRIPTION OF THE EMBODIMENTS

The girdle has a curved, hemispherical or a spherical cap shape, in order to follow the curves of the belly of a pregnant woman.

In an embodiment, the girdle includes, on its sides, attachments for an elastic strip which passes behind the back of the pregnant woman.

Figure 2:
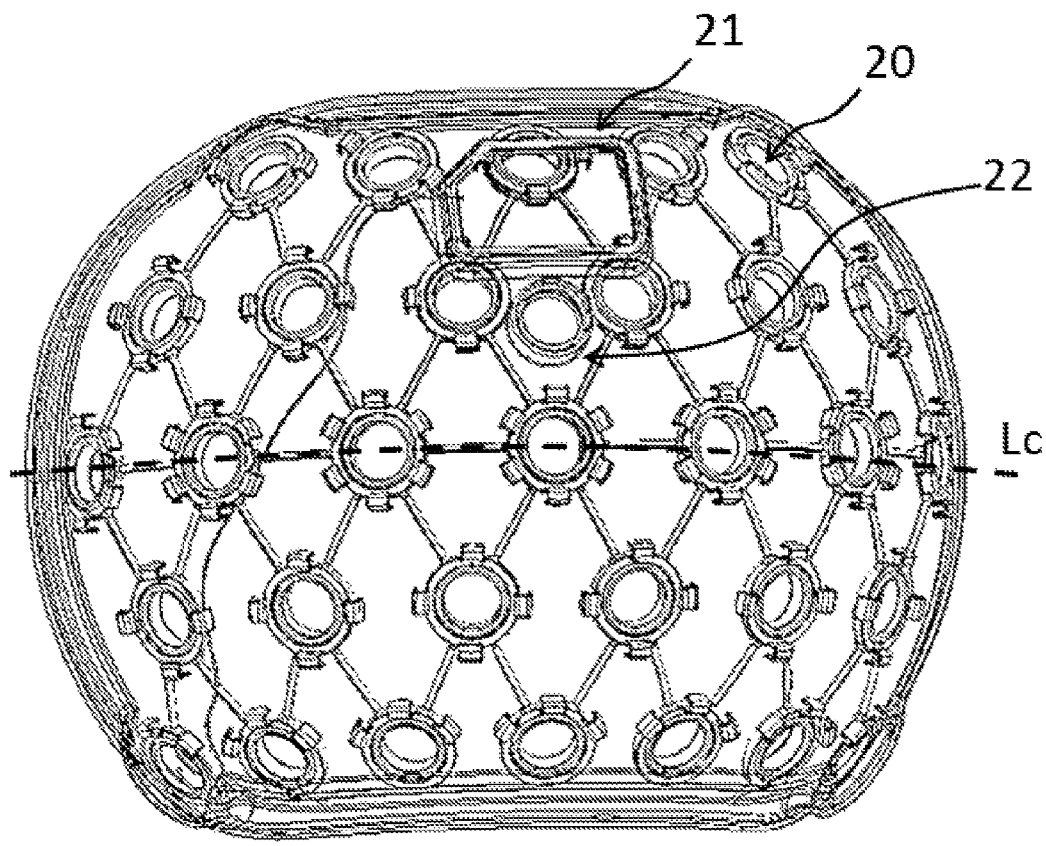
FIG. 2 represents the elements of FIG. 1 covered by a membrane composed of the first support layer and the second support layer.

In an embodiment, the spherical cap only includes a portion of the spherical cap, with substantially straight edges with roundings, see for example FIG. 2 at the top and bottom.

The overall dimensions of the product are: length=240 mm, width=190 mm, height=115 mm.

The girdle is composed of two following elements: an array of UST support cavities and a double membrane.

The array of UST support cavities has a centre distance of between 38 and 46 mm. In the example represented above, the centre distance is 45 mm between 2 mesh elements with a tolerance of approximately ±0.2 mm.

The size of the array is 200 mm×310 mm with a tolerance of approximately ±1 mm. A tape measure can be used to obtain these results.

The double membrane consists of a first support layer made of elastic material and a second support layer also made of elastic material. A "membrane" is characterised by a substantially constant thickness.

The thickness of the elastic membrane is 1.5 mm. For this value, there is a tolerance of approximately ±0.2 mm.

The total size with the double membrane is: 230 mm×360 mm. For these values, there is a tolerance of approximately ±1 mm. A tape measure can be used to obtain these results.

The mechanical properties of the elastic material is silicone elastomer with:
  elongation at break (test method: ISO 37): 500 to 1000%
  good tensile strength at break,
  medical-grade silicone (biocompatible for skin contact)

Figure 1:
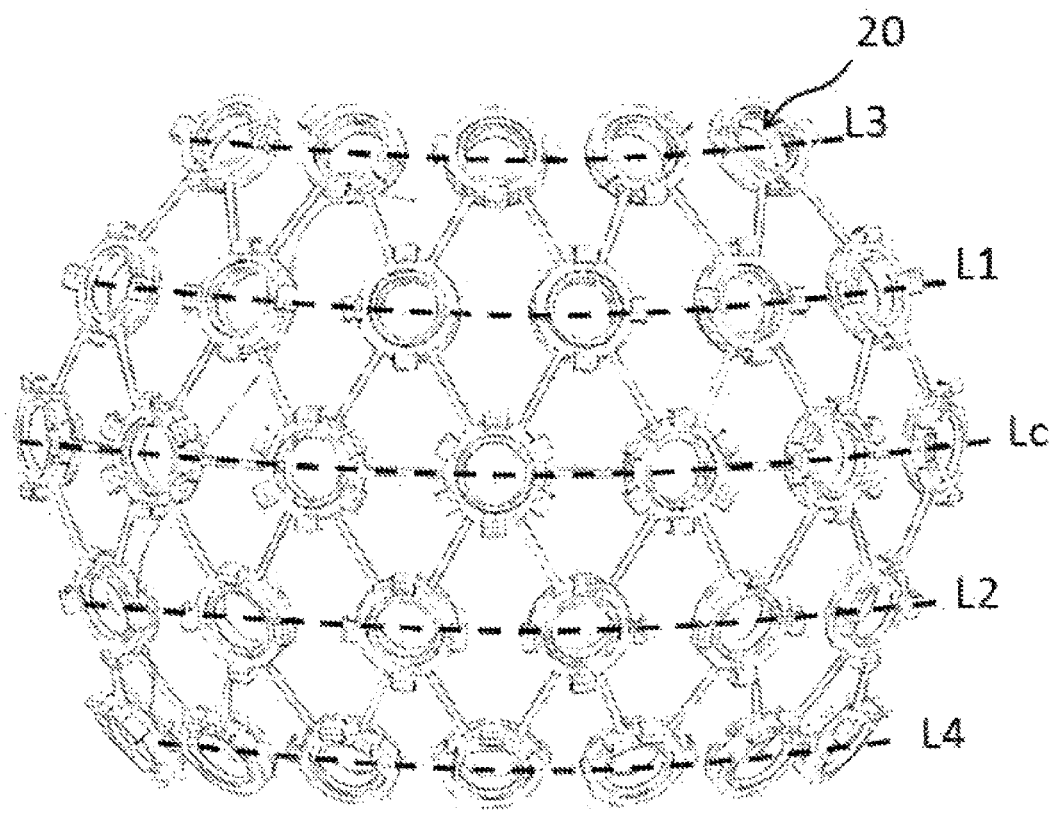
FIG. 1 represents a perspective view of a cardiotocography girdle portion, that is the subject of the present invention.

FIG. 1 shows an exemplary embodiment including the array of support cavities for thirty-one USTs. Each UST is clipped in the support cavities.

The support cavities 20 are arranged in the following manner:
  seven support cavities 20 follow a central line Lc defining a line of symmetry and each separated by a rigid link,
  six support cavities 20 follow a first line L1 parallel to the central line Lc, the first line L1 is proximal to the central line Lc and situated on one side, each support cavity 20 of the first line L1 is alternately positioned with two support cavities 20 of the central line Lc and connected to each of the two support cavities 20 of the central line Lc by a rigid link,
  six support cavities 20 follow a second line L2 parallel to the central line Lc, the second line L2 is proximal to the central line Lc and situated on the other side of the central line Lc, each support cavity 20 of the second line L2 is alternately positioned with two support cavities 20 of the central line Lc and connected to each of the two support cavities of the central line Lc by a rigid link,
  five support cavities 20 follow a third line L3 parallel to the central line, the third line L3 is distal from the central line and situated on the side of the first line L1, each support cavity 20 of the third line L3 is alternately positioned with two support cavities 20 of the first line L1 and connected to each of the two support cavities 20 of the first line L1 by a rigid link,
  five support cavities 20 follow a fourth line L4 parallel to the central line Lc, the fourth line L4 is distal from the central line Lc and situated on the side of the second line L2, each support cavity 20 of the fourth line L4 is alternately positioned with two support cavities 20 of the second line L2 and connected to each of the two support cavities 20 of the second line L2 by a rigid link,
  In this example, the rigid links have a length of 45 mm (distance between the centres of the transducers).

In this example, the longitudinal axis of each rigid link forms an angle of 60° with respect to a line parallel to the central line.

FIG. 2 shows the elements of FIG. 1 covered by a membrane composed of the first support layer made of elastic material and the second support layer made of elastic material. The support cavities 20 of the 31 USTs are shown.

This figure shows the connection box 21 which enables all the USTs to be connected to a control element. The connection box 21 makes it possible to read the data from the USTs or to transmit the data to a remote control element.

In another example, electrical wires connected to each UST come together to terminate in a coaxial cable which exits the girdle. This cable is connected to an electronics box which is included or not (other version) in the textile girdle. The electrical wires are located between the two membranes and are thus protected from water or any mechanical attack.

In another example, the connection box 21 is not on the girdle, but is remote therefrom.

The application of the girdle on the patient is made in the following manner: the patient's navel is substantially aligned with the first line L1.

FIG. 2 shows a through-hole 22 for positioning the navel of the patient.

The purpose of the through-hole 22 is to facilitate positioning by the patient.

The cardiotocography girdle has a through-hole (absence of through-material) enabling the user or the patient to have a visual cue and/or a tactile cue formed by the/her navel. This navel marker is located between the first line (L1) and the central line (Lc) and is in a central position of the cardiotocography girdle.

In an alternative, the through-hole 22 is positioned substantially in the middle of the first line L1.

Hence, the position of the USTs on the abdomen is identical from one examination to another for a given patient, due to this morphological marker.

Figure 3:
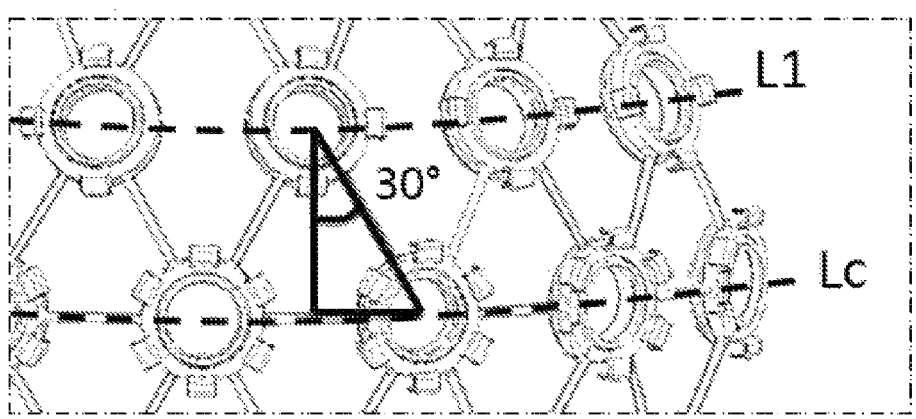
FIG. 3 represents an enlargement of a part of FIG. 1 in order to show an angle according to the exemplary embodiment of FIG. 1.

FIG. 3 shows an angle of approximately 30° formed by a right-angled triangle. The base is collinear with the axis of the central line, the hypotenuse corresponds to the rigid link and the side opposite the 30° angle corresponds to the perpendicular to the base.

The measurement is made from one support cavity centre to another support cavity centre. In this example, the hypotenuse is 45 mm.

Figure 4:
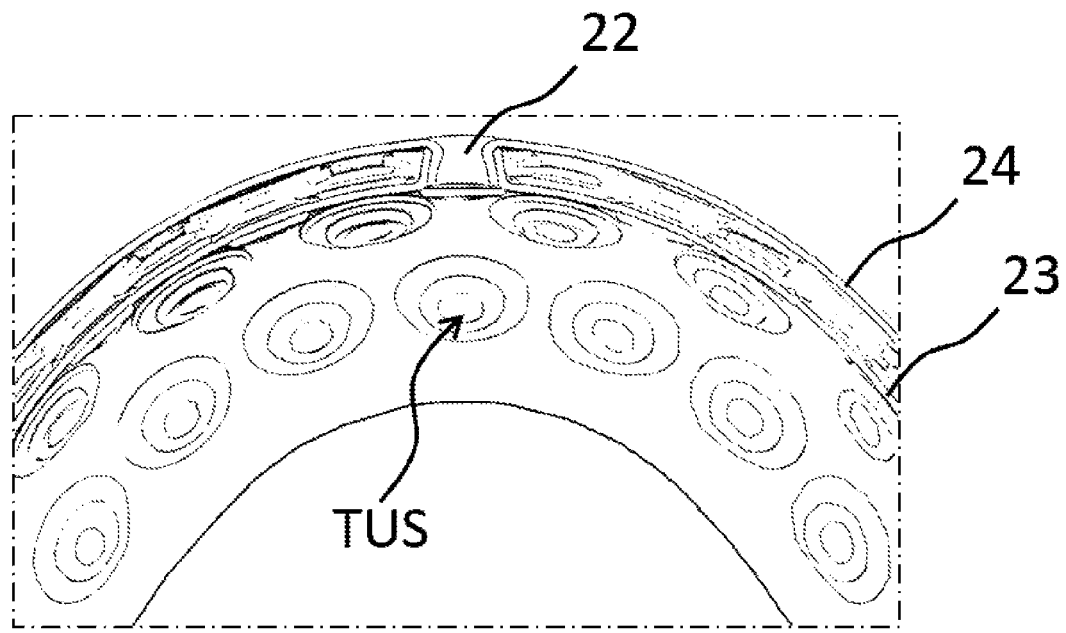
FIG. 4 represents a sectional view of a cardiotocography girdle, showing the first support layer and the second support layer, the marker hole and the USTs.

FIG. 4 shows a sectional view of a cardiotocography girdle. Visible are the first support layer 23 and the second support layer 24, the through-hole 22 (marker hole for the patient) and the USTs (the arrow points to a single UST, but a plurality of UST is visible.

Figure 5:
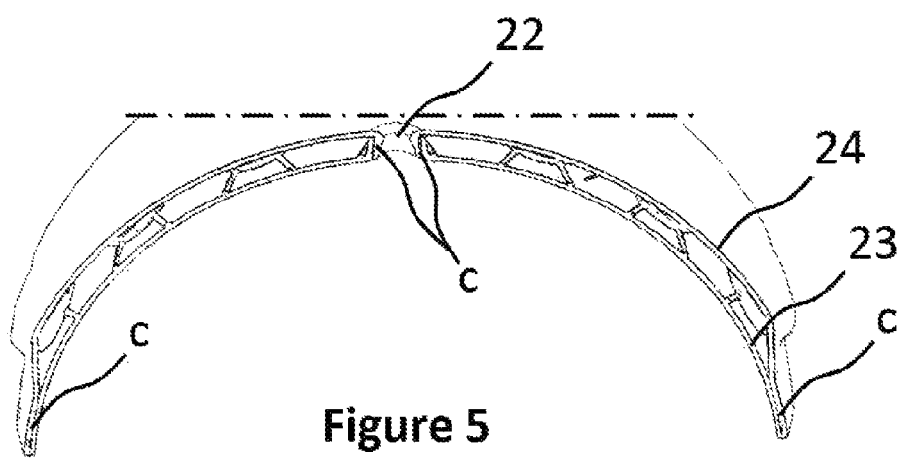
FIG. 5 represents another sectional view of a cardiotocography girdle, showing the adhesive bonding of the first support layer with the second support layer.

FIG. 5 shows another sectional view of a cardiotocography girdle, showing the adhesive bonding, denoted c, of the first support layer 23 and the second support layer 24.

Figure 6:
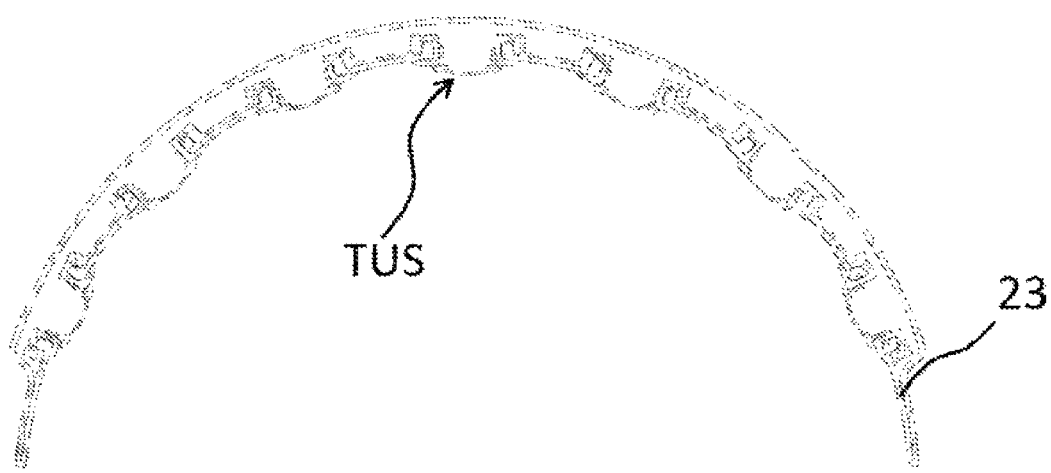
FIG. 6 represents another sectional view along the line LC.

FIG. 6 shows another sectional view along the line LC and visible in cross-section are the USTs (partial representation of the USTs), the first support layer 23 and the second support layer 24.

Figure 7:
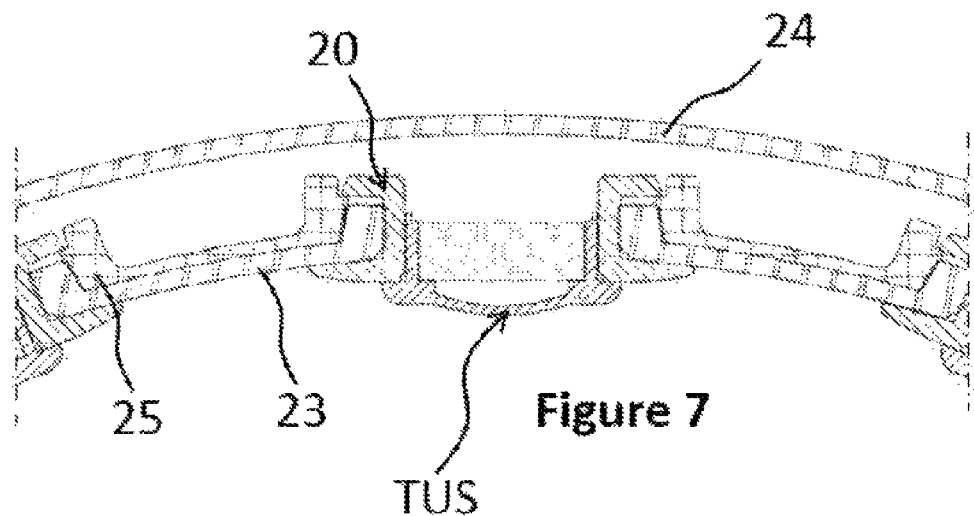
FIG. 7 represents a detailed view of the preceding section.

FIG. 7 shows a detailed view of the preceding section. Also visible are USTs in cross-section, the first support layer 23 and the second support layer 24.

Links between the support cavities 25 are represented and referenced.

In this figure, the UST is manifested by a rectangle which includes a receptacle visible in cross-section.

It should be remembered that the sealing of the technical part is ensured by the clipping of the USTs on to the support cavities 20 and by adhesive bonding of the two membranes to one another.

According to an embodiment, the assembly process enabling the sealing is performed by screwing with a seal, adhesively bonding with adhesive or adhesive tape, clipping, over moulding of the lower membrane on the support cavity array, ultrasonic welding of the USTs on the support cavity array. The sealing is produced according to this embodiment. However, any other manner of assembling the USTs in the support cavities allowing sealing is possible.

LIST OF REFERENCE SIGNS

TABLE 1

| References | Names |
|---|---|
| 20 | support cavity |
| 21 | connection box |

TABLE 1-continued

| References | Names |
|---|---|
| 22 | marker hole |
| 23 | first support layer |
| 24 | second support layer |
| 25 | links between the support cavities |
| USTs | ultrasound transducers |
| Lc | central line |
| L1 | first line |
| L2 | second line |
| L3 | third line |
| L4 | fourth line |

The invention claimed is:

1. A cardiotocography girdle in the form of a spherical dome wherein said cardiotocography girdle includes:
 a first support layer made of silicone,
 at least nineteen ultrasound transducers, referred to as USTs, which are positioned on the first support layer, each UST being positioned in a support cavity,
 a second support layer made of silicone and which encapsulates said USTs housed in the support cavities with the first support layer, wherein assembly is performed by adhesively bonding the first support layer to the second support layer, and
 a through-hole located substantially in a central position of the cardiotocography girdle.

2. The cardiotocography girdle according to claim 1, wherein said support cavities are arranged in the following manner, in which at least:
 five support cavities follow a central line defining a line of symmetry each separated by a rigid link,
 four support cavities follow a first line parallel to the central line, the first line is proximal to the central line and situated on one side, each support cavity of the first line is alternately positioned with two support cavities of the central line and connected to each of the two support cavities of the central line by a rigid link,
 four support cavities follow a second line parallel to the central line, the second line is proximal to the central line and situated on the other side of the central line, each support cavity of the second line is alternately positioned with two support cavities of the central line and connected to each of the two support cavities of the central line by a rigid link,
 three support cavities follow a third line parallel to the central line, the third line is distal from the central line and situated on the side of the first line, each support cavity of the third line is alternately positioned with two support cavities of the first line and connected to each of the two support cavities of the first line by a rigid link,
 three support cavities follow a fourth line parallel to the central line, the fourth line is distal from the central line and situated on the side of the second line, each support cavity of the fourth line is alternately positioned with two support cavities of the second line and connected to each of the two support cavities of the second line by a rigid link.

3. The cardiotocography girdle according to claim 1, wherein
 the thickness of the first layer or of the second support layer is between 1 and 2 mm.

4. The cardiotocography girdle according to claim 2, wherein the proximal distance between the first line and the central line or the second line and the central line is between 32 and 40 mm.

5. The cardiotocography girdle according to claim 2, wherein the distal distance between the third line and the central line or the fourth line and the central line is between 64 and 80 mm.

6. The cardiotocography girdle according to claim 2, wherein the rigid link between the central line and the first line or the central line and the second line forms an angle of between 50 and 70° with respect to the central line.

7. The cardiotocography girdle according to claim 2, wherein the rigid link between the first line and the third line, or between the second line and the fourth line, forms an angle between 50 and 70° with respect to the central line.

8. The cardiotocography girdle according to claim 2, wherein each rigid link has a length between 38 and 46 mm.

9. The cardiotocography girdle according to claim 2, wherein the through-hole is located between the first line and the central line.

\* \* \* \* \*